United States Patent
Fateh (10) Patent No.: US 10,152,867 B2
(45) Date of Patent: Dec. 11, 2018

(54) PORTABLE MANAGEMENT AND MONITORING SYSTEM FOR EYE DROP MEDICATION REGIMENT

(71) Applicant: Kali Care, Inc., Mountain View, CA (US)

(72) Inventor: Sina Fateh, Mountain View, CA (US)

(73) Assignee: KALI CARE, INC., Mountain View, CA (US)

( * ) Notice: Subject to any disclaimer, the term of this patent is extended or adjusted under 35 U.S.C. 154(b) by 748 days.

(21) Appl. No.: 13/844,233

(22) Filed: Mar. 15, 2013

(65) Prior Publication Data

US 2014/0276476 A1 Sep. 18, 2014

Related U.S. Application Data

(60) Provisional application No. 61/717,559, filed on Oct. 23, 2012.

(51) Int. Cl.
*A61M 35/00* (2006.01)
*G08B 21/02* (2006.01)
*A61F 9/00* (2006.01)

(52) U.S. Cl.
CPC ............ *G08B 21/02* (2013.01); *A61F 9/0026* (2013.01); *A61F 9/0008* (2013.01)

(58) Field of Classification Search
CPC .............................. A61F 9/0026; A61F 9/0008
USPC .................................. 604/289, 290, 295, 298
See application file for complete search history.

(56) References Cited

U.S. PATENT DOCUMENTS

| 5,152,424 A | 10/1992 | Weinreb et al. |
| 7,949,426 B2 | 5/2011 | Handfield et al. |
| 8,998,861 B2 | 4/2015 | Fateh |
| 9,728,068 B2 | 8/2017 | Engelhard et al. |
| 2004/0039355 A1* | 2/2004 | Gonzalez ............... A61F 9/0008 604/298 |
| 2004/0204674 A1* | 10/2004 | Anderson ........... A61M 5/1723 604/66 |
| 2007/0024465 A1 | 2/2007 | Howell et al. |

(Continued)

FOREIGN PATENT DOCUMENTS

| CN | 1759398 A | 4/2006 |
| EP | 1656923 A1 | 5/2006 |

(Continued)

OTHER PUBLICATIONS

Translation of EP1656923A1, Hermann et al., Oct. 12, 2005.*

(Continued)

*Primary Examiner* — Andrew J Mensh
(74) *Attorney, Agent, or Firm* — Perkins Coie LLP (57) ABSTRACT

Systems and methods for medication management are provided. Some embodiments provide for a portable medication management and monitoring system for eye drop instillation in ocular chronic conditions. At least one embodiment includes a device having one or more of the following elements: (a) a jacket that goes around an eye drop bottle; (b) tactile sensors to detect the user's fingers and generate data to activate the system; (c) motion sensors to detect the motion of the medication bottle when it is grabbed and moved by the user; (d) a wireless communication module to send and receive data to a computer and portable communication devices; and/or (e) a compartment for holding the electronic components.

21 Claims, 7 Drawing Sheets

(56) References Cited

U.S. PATENT DOCUMENTS

| | | | |
|---|---|---|---|
| 2009/0045078 A1 | 2/2009 | Gelardi et al. | |
| 2009/0240215 A1 | 9/2009 | Humayun et al. | |
| 2009/0259204 A1 | 10/2009 | Galdeti et al. | |
| 2009/0306633 A1 | 12/2009 | Trovato et al. | |
| 2010/0286634 A1* | 11/2010 | Marx | A61F 9/0026 604/302 |
| 2011/0264028 A1* | 10/2011 | Ramdas | A61M 5/14248 604/20 |
| 2012/0143152 A1 | 6/2012 | Hunter et al. | |
| 2012/0222979 A1 | 9/2012 | Baym et al. | |
| 2014/0062918 A1 | 3/2014 | Chen et al. | |
| 2014/0081100 A1 | 3/2014 | Muhsin et al. | |
| 2014/0228783 A1 | 8/2014 | Kraft | |
| 2014/0257206 A1 | 9/2014 | Fateh | |
| 2014/0276476 A1 | 9/2014 | Fateh | |
| 2015/0173945 A1 | 6/2015 | Fateh et al. | |
| 2016/0220180 A1 | 8/2016 | Fateh | |
| 2016/0239635 A1 | 8/2016 | Fateh | |
| 2017/0173262 A1 | 6/2017 | Veltz | |
| 2017/0340846 A1 | 11/2017 | Gramann et al. | |
| 2017/0357775 A1 | 12/2017 | Ekin | |
| 2018/0042417 A1 | 2/2018 | Brown et al. | |

FOREIGN PATENT DOCUMENTS

| | | |
|---|---|---|
| GB | 2418049 A | 3/2006 |
| WO | 2004028420 A1 | 4/2004 |
| WO | 2013043607 A1 | 3/2013 |
| WO | 2014004437 A1 | 1/2014 |

OTHER PUBLICATIONS

International Search Report and Written Opinion for International Application No. PCT/US2013/066450 dated Feb. 14, 2014.
Extended European Search Report dated May 27, 2016 for EP Patent Application No. 13848685.7, 9 pages.
First Office Action dated Mar. 25, 2016, for Chinese Patent Application No. 201380067442.1, 21 pages.
International Search Report and Written Opinion dated Jun. 30, 2016, for International Application No. PCT/US2016/017563 filed Feb. 11, 2016, 7 pages.
International Search Report and Written Opinion dated May 19, 2016, for International Application No. PCT/US16/15784 filed on Jan. 29, 2016, 7 pages.
Non-Final Office Action dated Aug. 29, 2014 for U.S. Appl. No. 14/281,001 of Fateh, S. et al. filed May 19, 2014.
Notice of Allowance dated Jan. 13, 2015 for U.S. Appl. No. 14/281,001 of Fateh, S. et al. filed May 19, 2014.
U.S. Appl. No. 14/608,704 of Fateh., filed Jan. 29, 2015.
U.S. Appl. No. 14/621,293 of Fateh., filed Feb. 12, 2015.
Extended European Search Report dated Dec. 15, 2017 for European Patent Application No. 16744225.0, 9 pages.
Non-Final Office Action dated Mar. 30, 2018 for U.S. Appl. No. 14/621,293 of S. Fateh filed Feb. 12, 2015.
Notification of Registration and Granting a Patent Right dated Mar. 28, 2018, for Chinese Patent Application No. 201380067442.1, 10 pages.
Restriction Requirement dated Jan. 5, 2018 for U.S. Appl. No. 14/621,293 of Fateh, S. filed Feb. 12, 2015.
Second Office Action dated Feb. 21, 2017, for Chinese Patent Application No. 201380067442.1, 18 pages.
Supplementary European Search Report dated Oct. 9, 2017 for European Patent Application No. 16749887.2, 8 pages.
Third Office Action dated Sep. 19, 2017, for Chinese Patent Application No. 201380067442.1, 10 pages.
Final Office Action dated Jul. 26, 2018 for U.S. Appl. No. 14/621,293 of S. Fateh filed Feb. 12, 2015.
Non-Final Office Action dated Jul. 26, 2018 for U.S. Appl. No. 14/639,989 of Fateh, S., filed Mar. 5, 2015.
Restriction Requirement dated Jul. 2, 2018 for U.S. Appl. No. 14/608,704 of Fateh, S. filed Jan. 29, 2015.

* cited by examiner

PORTABLE MANAGEMENT AND MONITORING SYSTEM FOR EYE DROP MEDICATION REGIMENT

CROSS-REFERENCE TO RELATED APPLICATIONS

This application claims priority to U.S. Provisional Application Ser. No. 61/717,559 filed Oct. 23, 2012, which is incorporated herein by reference for all purposes.

TECHNICAL FIELD

Various embodiments of the present invention generally relate to medication management. More specifically, some embodiments of the present invention relate to systems and methods for portable management and monitoring of an eye drop medication regiment.

BACKGROUND

Approximately thirty percent of medication prescriptions are never filled. In addition, approximately fifty percent of medications for chronic disease are not taken as prescribed. This lack of adherence has dramatic effects on health. Non adherence has been estimated to cost the U.S. health care system $200 billion annually. In ophthalmology, the problem of noncompliance is particularly significant in the management of chronic conditions such as glaucoma where a strict adherence to the medication plan is vital for preventing visual loss and blindness. Almost seventy-five percent of patients admit to some form of noncompliant behavior, over thirty percent do not fill their prescriptions, and nearly fifty percent discontinue prescribed drops within six months.

While forgetfulness is one barrier to medication adherence, it is not the only barrier. In addition, taking the medication at the wrong time, stopping too early or taking the wrong dose also represent other serious barriers. Unfortunately, there are no effective systems for managing adherence to a medication plan which can be vital for preventing visual loss and/or blindness.

BRIEF DESCRIPTION OF THE DRAWINGS

Embodiments of the present invention will be described and explained through the use of the accompanying drawings in which.

The drawings have not necessarily been drawn to scale. For example, the dimensions of some of the elements in the figures may be expanded or reduced to help improve the understanding of the embodiments of the present invention. Similarly, some components and/or operations may be separated into different blocks or combined into a single block for the purposes of discussion of some of the embodiments of the present invention. Moreover, while the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various embodiments of the present invention generally relate to medication management. More specifically, some embodiments of the present invention relate to systems and methods for portable management and monitoring of an eye drop medication regiment. In some embodiments, a portable medication management and monitoring system is disclosed for eye drop instillation in ocular chronic conditions. Various embodiments of the system provide for a management care system that reminds (e.g., with visual or audible indicators) the user of the time and date of each eye drop instillation, notifies the user if any doses are being missed, records for medication management purposes each instillation, sends progress reports to the user and/or third-parties (family members or doctors), and provides a refill notification to the pharmacist. One advantage of the reminder system provided by embodiments of the present invention is the improvement in compliance with medication treatment routines and is advantageous for people who struggle remembering to instill their eye drops. The solution also improves the clinical outcomes.

Various embodiments of the device can include one or more of the following components: (a) a jacket that goes around an eye drop bottle; (b) tactile sensors to detect the user's fingers and generate data to activate the system; (c) motion sensors to detect the motion of the medication bottle when it is grabbed and moved by the user; (d) a wireless communication module to send and receive data to a computer and a portable communication device; and/or (e) a compartment for holding the electronic components.

Various embodiments of the present invention are compatible with a web-based medication adherence system. A user can log into the web-based system and load data regarding a medication regiment manually on a web site. This information can optionally be shared or sent to an eye care provider (e.g., for tracking medication adherence) or pharmacist (e.g., for automatic medication refills). In addition, some embodiments of the present invention provide for different types of external and/or device-based reminding systems such as automated text messaging, phone calls, or auditory (beeper) and visual reminders such as a flashing or changing color LED light. For example, in one embodiment, the text messaging system may allow a profile to be created the first time a user logs into the web-based system. The system may request or automatically populate information such as a phone number or email address Various embodiments of the present invention provide for proactive and reactive reminding systems that allow users to send back confirmation receipts (e.g., a text reply or simply an intuitive gesture using the mobile phone). For example, moving the mobile phone to simulate the gesture of eye drop instillation would say, "Yes, I took my eye drop". Engaging the patient in the process improves and sustains the motivation for medication adherence. The system uses a small battery or can be charged on a small station.

In the following description, for the purposes of explanation, numerous specific details are set forth in order to provide a thorough understanding of embodiments of the present invention. It will be apparent, however, to one skilled in the art that embodiments of the present invention may be practiced without some of these specific details. While, for convenience, embodiments of the present invention are described with reference to portable medication management, embodiments of the present invention are equally applicable to various other types of liquid dispensing and tracking needs outside of the medical industry.

Moreover, the techniques introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions that may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other types of media/machine-readable mediums suitable for storing electronic instructions.

Terminology

Brief definitions of terms, abbreviations, and phrases used throughout this application are given below.

The terms "connected" or "coupled" and related terms are used in an operational sense and are not necessarily limited to a direct physical connection or coupling. Thus, for example, two devices may be coupled directly, or via one or more intermediary media or devices. As another example, devices may be coupled in such a way that information can be passed therebetween, while not sharing any physical connection with one another. Based on the disclosure provided herein, one of ordinary skill in the art will appreciate a variety of ways in which connection or coupling exists in accordance with the aforementioned definition.

The phrases "in some embodiments," "according to some embodiments," "in the embodiments shown," "in other embodiments," and the like generally mean the particular feature, structure, or characteristic following the phrase is included in at least one implementation of the present invention, and may be included in more than one implementation. In addition, such phrases do not necessarily refer to the same embodiments or different embodiments.

If the specification states a component or feature "may", "can", "could", or "might" be included or have a characteristic, that particular component or feature is not required to be included or have the characteristic.

The term "module" refers broadly to a software, hardware, or firmware (or any combination thereof) component. Modules are typically functional components that can generate useful data or other output using specified input(s). A module may or may not be self-contained. An application program (also called an "application") may include one or more modules, or a module can include one or more application programs.

General Description

Figure 1:
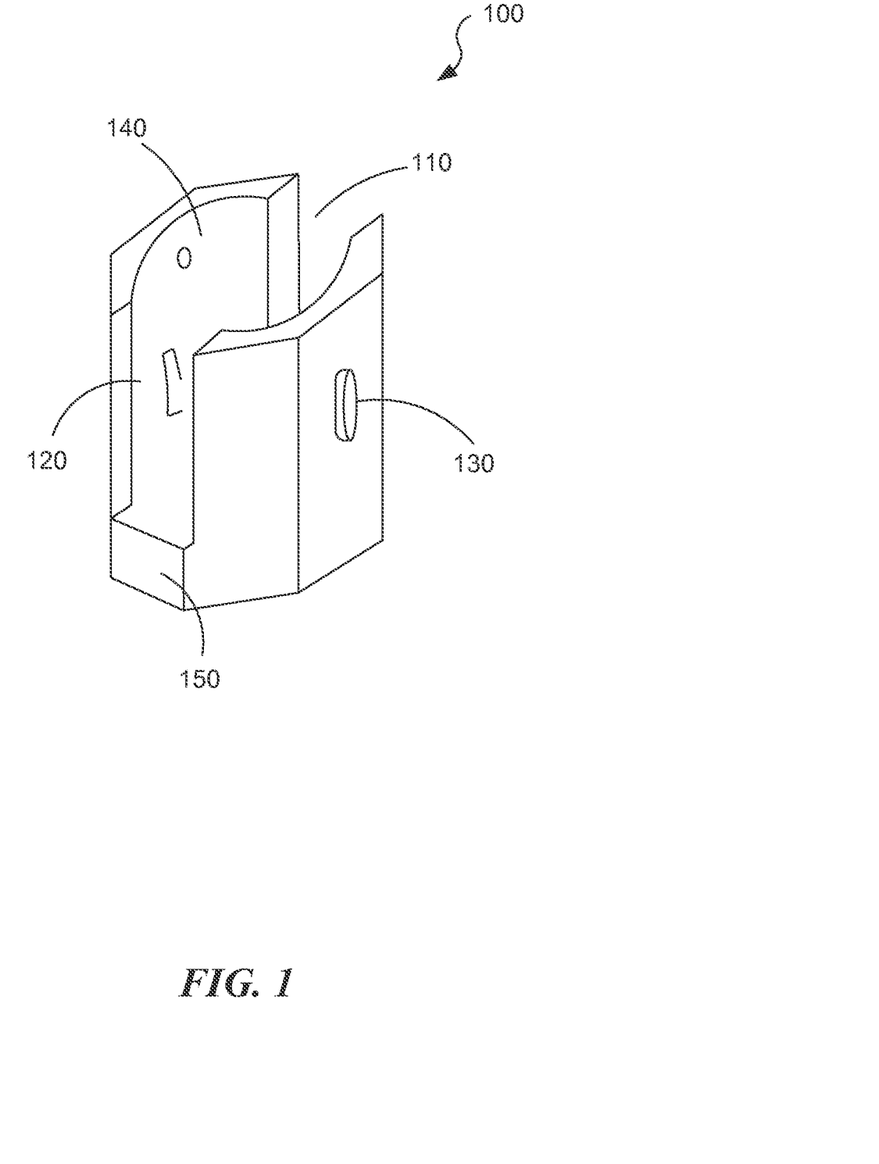
FIG. 1 illustrates an example of a medication management device in accordance with one or more embodiments of the present invention.

FIG. 1 illustrates an example of a medication management device in accordance with one or more embodiments of the present invention. As illustrated in FIG. 1, the medication management device provides a jacket or expansion pack 100 to enclose a bottle of eye drops within opening 110. Jacket 100 can include a wing pressure mechanism 120, a tactile sensor 130, a drop sensor 140, and an electronic module compartment 150. Wing pressure mechanism 120 provides a mechanism for securing a bottle within opening 110 of jacket 100. In other embodiments, other mechanisms may be used. For example, inserts of different sizes may be sized to fit securely within opening 110 of jacket 100, and at the same time, provide a smaller opening for securing the bottle. In other cases, different materials may be used to line jacket 100 that are flexible enough to allow for insertion of bottles of varying sizes. Still yet, various mechanical levers and gripping members may be used to secure the bottle within jacket 100.

Tactile sensor 130 can be used to provide a touch input interface (e.g., to detect the finger of a user). The user's touch can then activate/deactivate (i.e., turn on-off) the device. In some embodiments, the sensors can also detect and record other types of data such as pulse and heart rate. Drop detector sensor 140 can detect when a drop of liquid leaves the bottle. Drop sensor 140 could be an optical (e.g., LED/phototransistor) sensor capable of detecting if a drop has been released from the bottle. In these cases, when a drop is released from the bottle, the drop will refract a beam and produce a signal on the output. Drop sensor 140 may be placed at the top of the expansion pack and could be activated only in a specific position of the bottle to conserve power.

Electronic module compartment 150 can house one or more modules and/or components (e.g., processors, communication devices, integrated electronics, memory storage devices, batteries, etc.) of the medication management device. For example, in some embodiments, electronic module compartment 150 can include a gesture recognition module. The gesture recognition module can be used for detecting and providing the hand and bottle motion and position. In order to avoid false and unwanted motion measurement, in some embodiments, the gesture recognition module may be activated only when the tactile sensors detect touch by a user's finger.

As another example, a wireless communication module can be used to send and receive data to and from a computer and portable communication devices. An embedded controller module can include signal preprocessing electronics. Still yet, the device may include Wi-Fi, Bluetooth, cellular, or other wireless technology to send and load data to a mobile device or computer.

Figure 2:
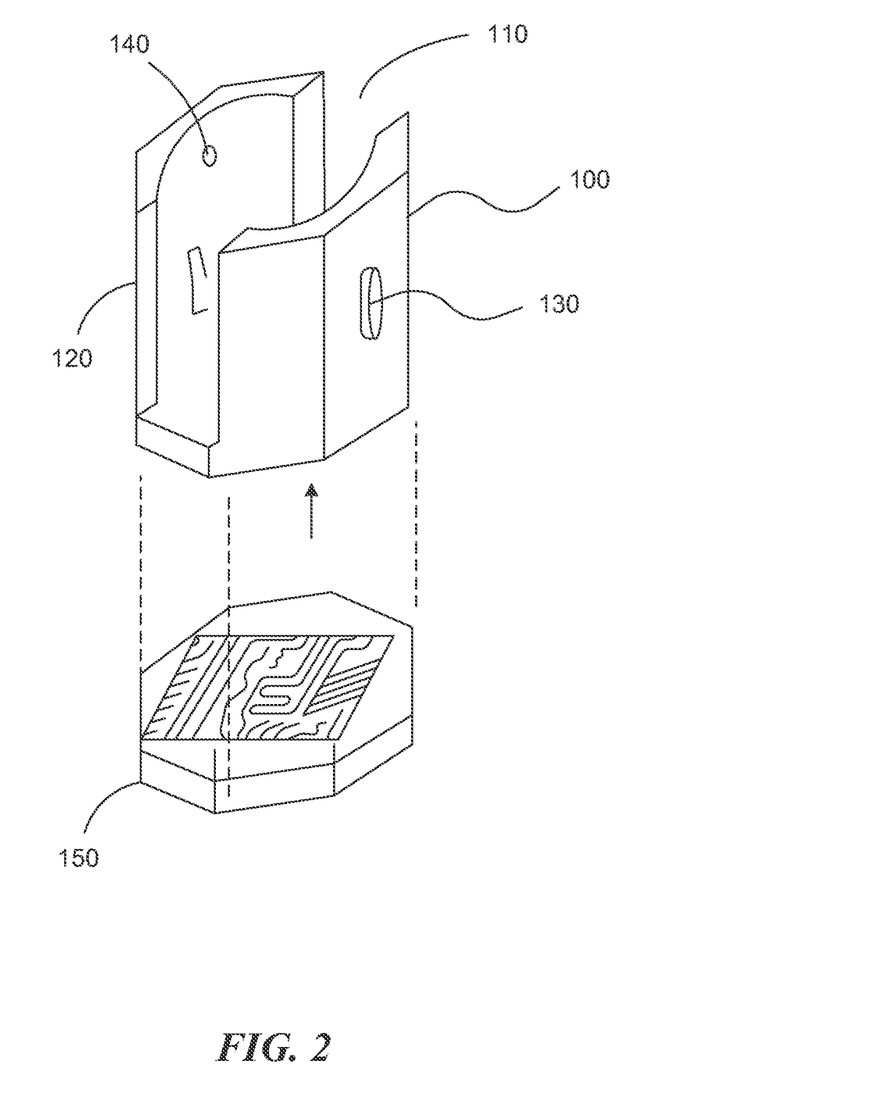
FIG. 2 is an expanded view of a medication management device that may be used in accordance with various embodiments of the present invention.

In some embodiments, jacket 100 may have integrated electronics and components embedded throughout. As illustrated in FIG. 2, electronic module compartment 150 can be removable from jacket 100. As a result, some embodiments provide for a plurality of jackets, each having openings of different sizes and lengths to hold different sized bottles. The jackets can be removed and interchanged with the electronic module compartment. The jackets can include mechanical, electrical, or electromechanical sensors for detecting that a bottle is present within the jacket. For example, in some embodiments, optical components or switches may be used to detect that a bottle is present within the jacket.

Figure 3:
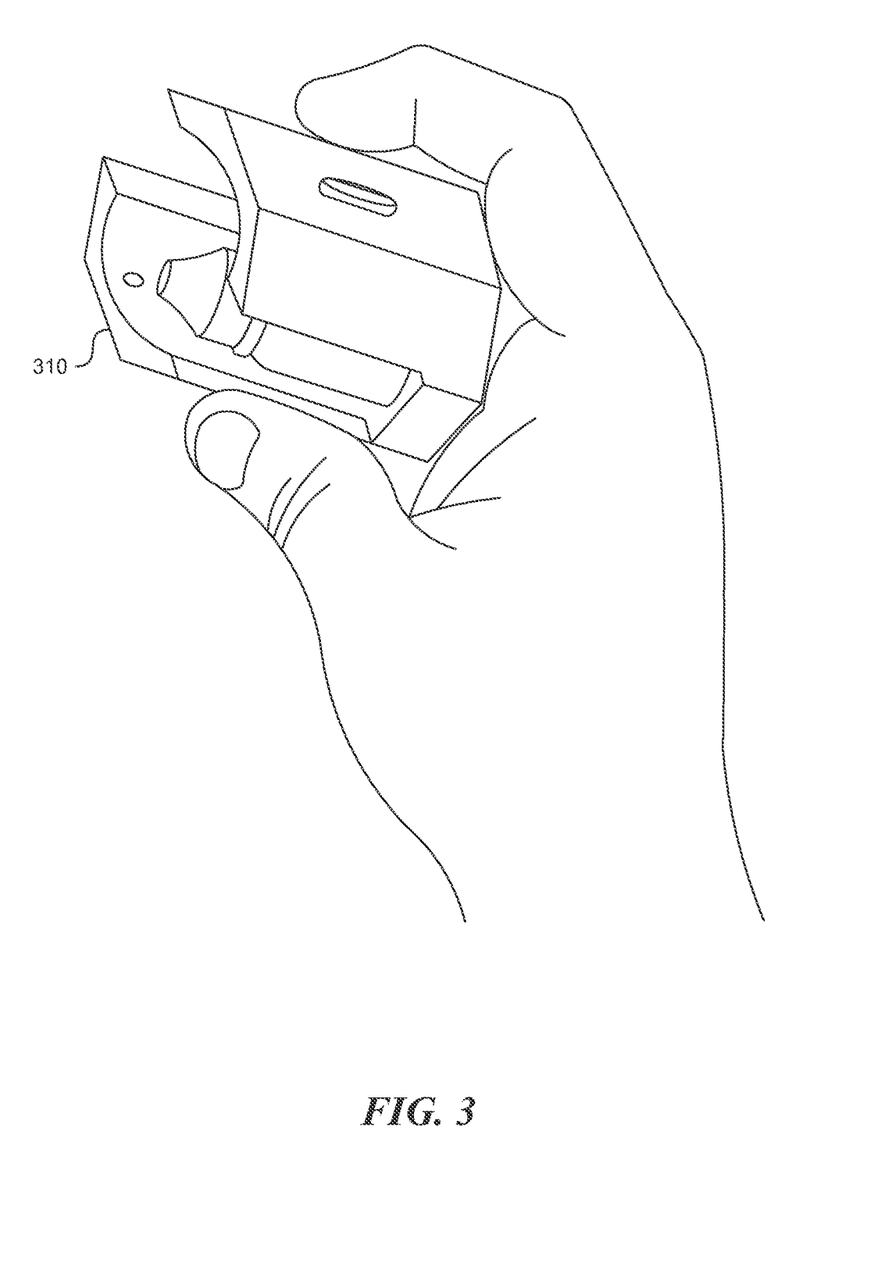
FIG. 3 is a side view of a user tilting a medication management device in accordance with some embodiments of the present invention.
Figure 4:
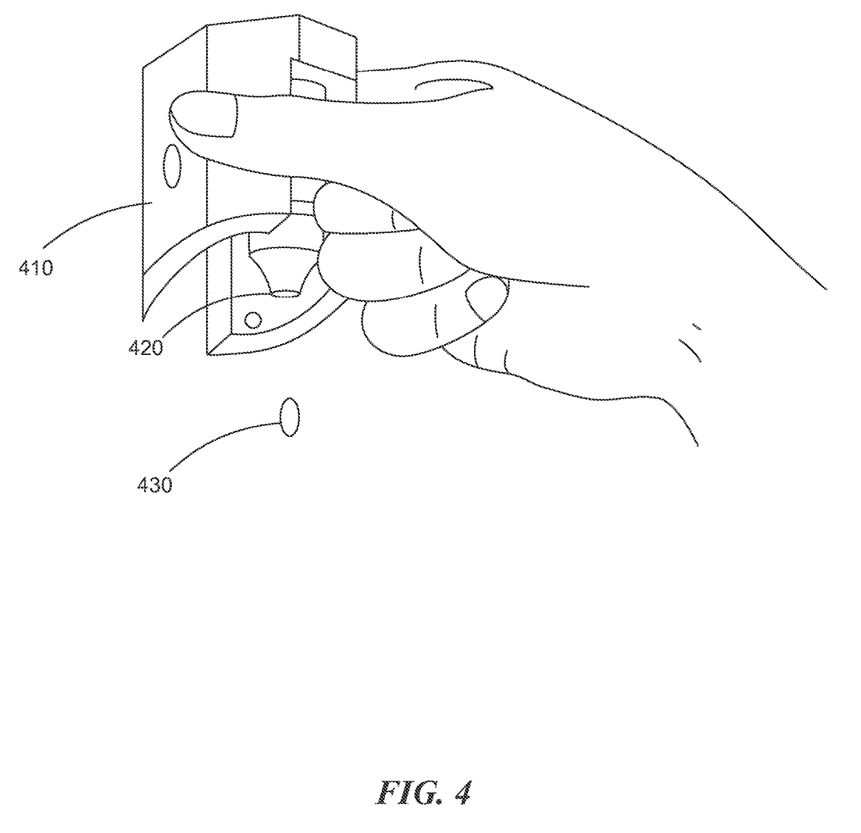
FIG. 4 is a view of a user using a medication management device to distribute eye drops in accordance with one or more embodiments of the present invention.

FIG. 3 is a side view of a user tilting a portable medication management device 310 in accordance with some embodiments of the present invention. Once a bottle is placed within the device and a user begins to interact with portable medication management device 310, various subsystems can be activated for tracking the user's activity. For example, when the user interacts (e.g., touches, moves, etc.) with the device, various sensors (e.g., drop sensors) can be activated. Then as the user tilts portable medication management device 410 upside down, as illustrated in FIG. 4, the sensors can determine if eye drop 430 was distributed from bottle 420.

Figure 5:
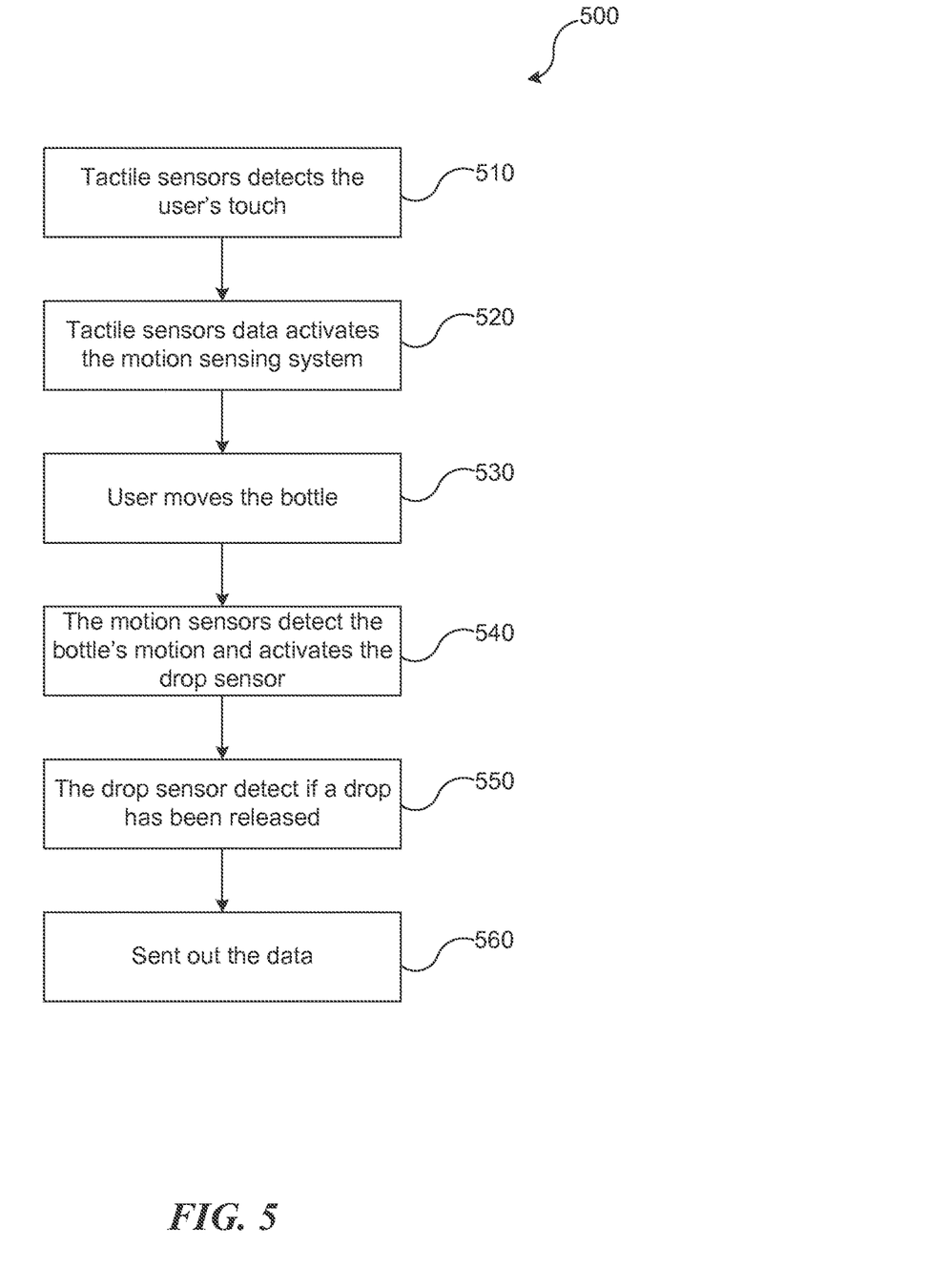
FIG. 5 is a flowchart illustrating a set of exemplary operations for using a medication management device in accordance with some embodiments of the present invention.

FIG. 5 is a flowchart illustrating a set of exemplary operations 500 for using a medication management device in accordance with some embodiments of the present invention. As illustrated in FIG. 5, detection operation 510 uses one or more tactile sensors to detect a touch from the user. The tactile sensors may be used to produce tactile sensor data. The data can include information regarding amount of pressure on each sensor, length of touch, touching patterns, and/or other information. Upon detection of a touch from the user, the tactile sensor data can be used to activate a motion-sensing subsystem within the device. In some embodiments, for example, the motion-sensing subsystem may only be activated when a touch lasting more than a predetermined length of time (e.g., one second) is detected.

As the user moves the bottle during movement operation 530, the motion sensors (e.g., accelerometers, cameras, optical components, etc.) are capable of detecting the bottle's motion and activating a drop sensor during activation operation 540. In some embodiments, if no movement is detected within a certain amount of time (e.g., ten seconds), the motion detectors may be deactivated. Once the drop sensor is activated, monitoring operation 550 determines if a drop has been released from the bottle. Data (e.g., number of drops, time, date, etc.) may then be transmitted to a medication adherence system or a communications device for processing and/or tracking.

Figure 6:
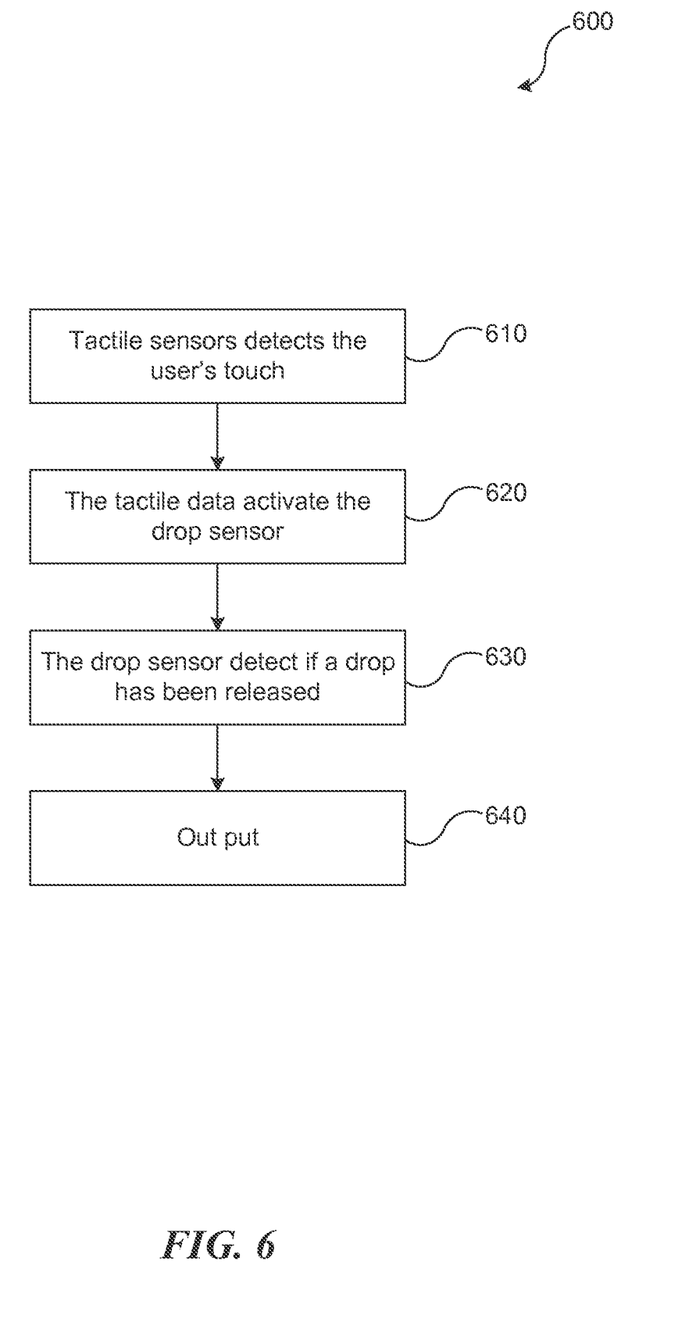
FIG. 6 is a flowchart illustrating a set of exemplary operations for determining if an eye drop has been released in accordance with some embodiments of the present invention.

FIG. 6 is a flowchart illustrating a set of exemplary operations 600 for determining if an eye drop has been released in accordance with some embodiments of the present invention. As illustrated in FIG. 6, one or more tactile sensors can be used to detect user interaction with the medication management device during detection operation 610. In accordance with various embodiments, the tactile sensors may be actively monitoring for input from the user. In other embodiments, the tactile sensors may be a mechanical switch or button that requires a specific type of pressure, motion, or interaction in order to trigger a detection event having a set of tactile data. This data can be used to activate one or more drop sensors during activation operation 620. Determination operation 630 then determines if the drop sensor detects a drop being released from the bottle. Information regarding the drop (e.g., medication type, time of day, date, etc.) can then be transmitted to a medication adherence system during output operation 640. Output operation 640 may send updates automatically on a predetermined schedule or upon detection of an event. In some cases, wireless transmissions (e.g., cellular, Bluetooth, etc.) can be used to transmit the data.

Figure 7:
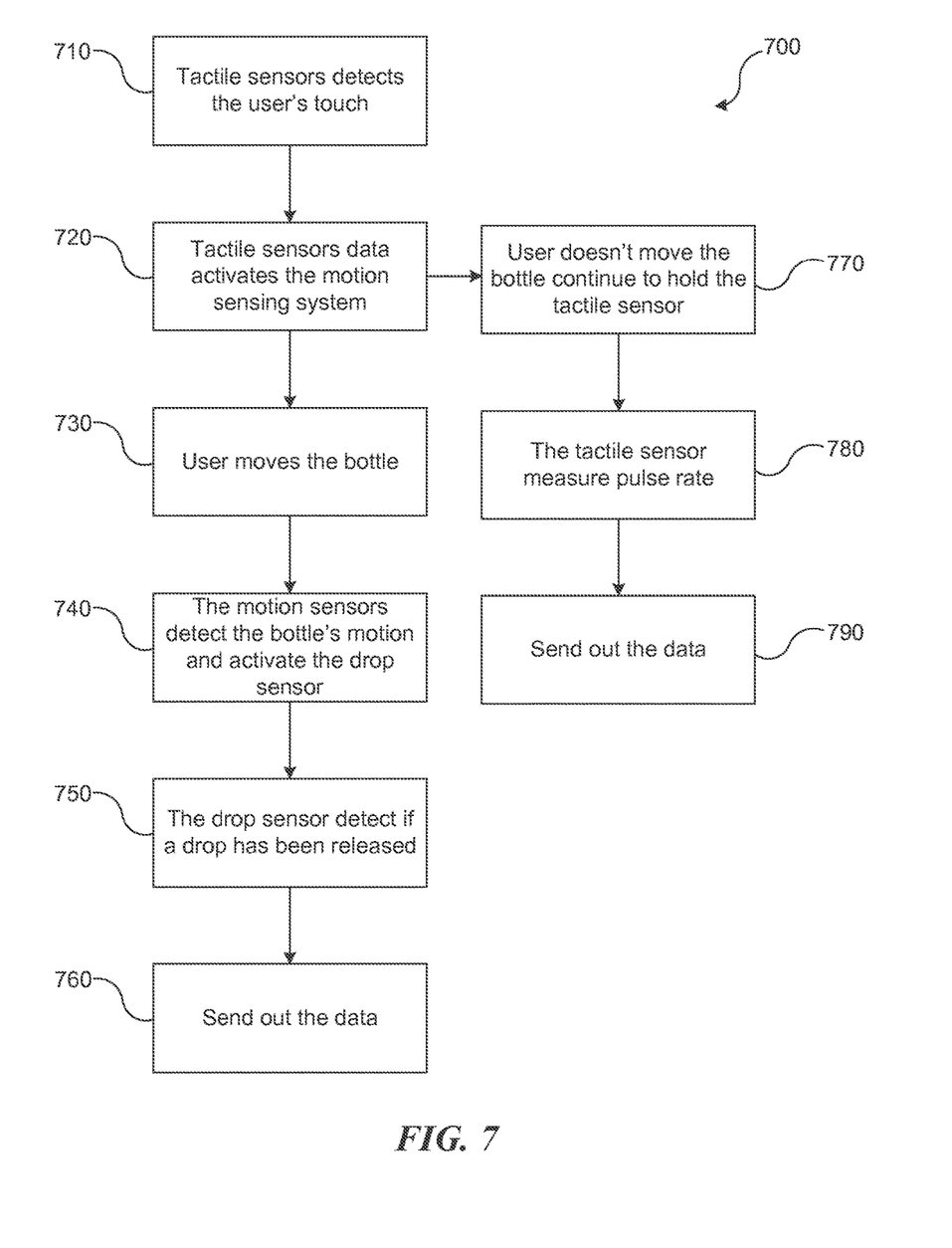
FIG. 7 is a flowchart illustrating a set of exemplary operations for measuring medication adherence and user vitals in accordance with some embodiments of the present invention.

FIG. 7 is a flowchart illustrating a set of exemplary operations for measuring medication adherence and user vitals in accordance with some embodiments of the present invention. As illustrated in FIG. 7, detection operation 710 uses one or more tactile sensors to detect a touch from the user. The tactile sensors may be used to produce tactile sensor data. As discussed above, the data can include information regarding amount of pressure on each sensor, length of touch, touching patterns, and/or other information. Upon detection of the touch from the user, the tactile sensor data can be used to activate a motion-sensing subsystem within the device during motion-sensing activation operation 720.

As the user moves the bottle during movement operation 730, the motion sensors are capable of detecting the bottle's motion and activating a drop sensor during activation operation 740. Once the drop sensor is activated, monitoring operation 750 determines if a drop has been released from the bottle. Drop data (e.g., number of drops, time, date, etc.) may then be transmitted to a medication adherence system or a communications device for processing and/or tracking.

If motion-sensing operation 720 does not detect any movement of the bottle by the user, holding operation 770 determines if the user continues to hold the one or more tactile sensors (e.g., for more than five or ten seconds). Once a holding threshold has been exceeded, a pulse rate measuring algorithm may be activated during pulse rate activation operation 780 to measure the user's pulse rate, heart rate, or even blood chemistry. The pulse rate data can then be transmitted to another device and/or monitoring system.

Embodiments of the present invention include various steps and operations, which have been described above. A variety of these steps and operations may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware.

In conclusion, various embodiments of the present invention provide novel systems, methods and arrangements for management and monitoring of an eye drop medication regiment. While detailed descriptions of one or more embodiments of the invention have been given above, various alternatives, modifications, and equivalents will be apparent to those skilled in the art without varying from the spirit of the invention. For example, while the embodiments described above refer to particular features, the scope of this invention also includes embodiments having different combinations of features and embodiments that do not include all of the described features.

What is claimed is:

1. A method comprising:
   securing an eye drop bottle within a jacket of a medication management device using a pressure mechanism;
   generating, by the medication management device, tactile sensor data to enable detection of a touch of a tactile sensor by a user;
   based on the tactile sensor data, activating, by the medication management device, a motion sensor to collect motion sensor data to enable detection of movement of the medication management device;
   responsive to detecting movement of the medication management device within a certain amount of time, activating, by the medication management device, a drop sensor to collect drop data to enable detection of a release of a drop of liquid from the eye drop bottle; and
   based on the drop data, sending, by the medication management device, data associated with the drop data to a medication adherence system.

2. The method of claim 1, further comprising:
responsive to not detecting movement of the medication management device within the certain amount of time, causing, by the medication management device, the tactile sensor to measure a pulse rate of the user.

3. The method of claim 1, further comprising:
recording the data associated with the drop data.

4. The method of claim 1, wherein the medication adherence system is a system for monitoring adherence of the user to a medication plan.

5. The method of claim 4, wherein the medication adherence system is associated with any of an eye care provider or a pharmacist.

6. The method of claim 1, further comprising:
determining a time and a date that the user should place one or more drops of liquid within an eye of the user.

7. The method of claim 6, further comprising:
based on the time and the date, generating an auditory reminder or a visual reminder that the user should place the one or more drops of the liquid within the eye of the user.

8. The method of claim 6, further comprising:
notifying the user, based on the time, the date, and the drop data, that a dose of a medication was missed.

9. The method of claim 1, further comprising:
based on the drop data, sending a refill notification to a pharmacist.

10. The method of claim 1, wherein the tactile sensor data specifies a pressure, a motion, or an interaction.

11. The method of claim 1, wherein the drop sensor is an optical sensor capable of detecting when the drop of liquid is released from the eye drop bottle.

12. The method of claim 7, wherein the medication management device includes one or more light-emitting diodes capable of providing the visual reminder to the user, one or more speakers capable of providing the auditory reminder to the user, or both.

13. The method of claim 7, further comprising:
enabling the user to elect whether the medication management device provides the visual reminder or the auditory reminder.

14. A method comprising:
generating, by a tactile sensor of a medication management device, tactile sensor data to enable detection of a touch of the tactile sensor by a user;
based on the tactile sensor data, activating a motion sensor to collect motion sensor data to enable detection of movement of the medication management device;
responsive to detecting movement of the medication management device within a certain amount of time, activating a drop sensor of the medication management device to collect drop data to enable detection of a release of a drop of liquid from a bottle that is secured within a jacket of the medication management device using a pressure mechanism; and
based on the drop data, sending data associated with the drop data across a network to a medication adherence system,
wherein the medication adherence system is configured to monitor the user's adherence to a medication regimen based on the data.

15. The method of claim 14, further comprising:
responsive to not detecting movement of the medication management device within the certain amount of time, measuring, by the tactile sensor, a pulse rate, a heart rate, or a blood chemistry of the user.

16. The method of claim 14, wherein the pressure mechanism includes a wing pressure mechanism.

17. The method of claim 14, further comprising:
storing, by the medication management device, at least some of the drop data within a memory,
wherein the memory includes information related to the medication regimen of the user.

18. The method of claim 17, wherein the information includes one or more of a time, a date, a quantity, or a type of medication that is to be dispensed by the medication management device.

19. The method of claim 18, further comprising:
comparing, by the medication management device, the drop data to the information related to the medication regimen; and
based on said comparing, determining, by the medication management device, whether the user has adhered to the medication regimen.

20. The method of claim 15, further comprising:
sending, by the medication management device, information regarding the pulse rate, the heart rate, or the blood chemistry of the user to the medication adherence system.

21. The method of claim 14, further comprising:
monitoring a spatial position of the medication management device,
wherein the drop sensor is not activated unless the spatial position of the medication management device matches a specified position.

* * * * *